United States Patent [19]

Rimondi et al.

[11] Patent Number: 5,784,283
[45] Date of Patent: *Jul. 21, 1998

[54] SYSTEM FOR OPTIMIZING CURE ASSURING QUALITY OF REVERSION SUSCEPTIBLE RUBBER ARTICLES

[75] Inventors: Giovanni Rimondi, Guilford, Conn.; William James Toth, Clinton, Ohio

[73] Assignee: Pirelli Coordinamento Pneumatici S.p.A., Milan, Italy

[*] Notice: The term of this patent shall not extend beyond the expiration date of Pat. No. 5,680,315.

[21] Appl. No.: 904,944

[22] Filed: Aug. 1, 1997

Related U.S. Application Data

[63] Continuation of Ser. No. 408,148, Mar. 20, 1995, Pat. No. 5,680,315.

[51] Int. Cl.$^6$ .............................. G06F 19/00; B29C 45/76
[52] U.S. Cl. .............................. 364/475.03; 364/475.04; 425/170; 264/40.1
[58] Field of Search .................. 364/475.02–475.05, 364/551.01, 557, 40.1–40.3; 425/170

[56] References Cited

U.S. PATENT DOCUMENTS

| | | |
|---|---|---|
| 3,397,583 | 8/1968 | Sperberg . |
| 3,819,915 | 6/1974 | Smith . |
| 4,344,142 | 8/1982 | Diehr, II et al. . |
| 4,371,483 | 2/1983 | Mattson . |
| 4,551,807 | 11/1985 | Hsich et al. . |
| 4,810,438 | 3/1989 | Webster et al. . |
| 4,819,177 | 4/1989 | Jurgensen . |
| 5,055,245 | 10/1991 | Hisatomi et al. . |
| 5,125,821 | 6/1992 | Saeki et al. . |
| 5,207,956 | 5/1993 | Kline et al. . |
| 5,219,498 | 6/1993 | Keller et al. . |
| 5,345,397 | 9/1994 | Handel et al. . |
| 5,453,226 | 9/1995 | Kline et al. . |

FOREIGN PATENT DOCUMENTS

| | | |
|---|---|---|
| 0 516 367 A2 | 5/1992 | European Pat. Off. . |
| 96104359 | 8/1996 | European Pat. Off. . |
| 26 12 253 A1 | 10/1977 | Germany . |
| 2 187 291 | 9/1987 | United Kingdom . |
| 2 280 516 | 2/1995 | United Kingdom . |

OTHER PUBLICATIONS

M.R. Kamal, et al. "Integrated Thermo–Rheological Analysis Of The Cure Of Thermosets", *31st Annual Technology Conference, SPE*, 187, Montreal, Canada, May 1973.

Malkin, A.Y., "The Macrokinetics and Rheokinetics of the Hardening of Oligimers," *Russian Chemical Reviews*, vol. 54, No. 3, 1985, p. 293.

Kamal, M.R. "Thermoset Characterization for Moldability Analysis," *Polymer Engineering and Science*, vol. 14, No. 3, 1974, p. 231.

Gehman, S.D., Maxey, F.S., and Ogilby, S.R., "Vulcameter Determination of Best Cure," *Rubber Chemistry and Technology*, vol. 38, No. 4, 1965, pp. 757–768.

Toth, W.J., Chang, J.P., Zanichelli, C., "Finite Element Evaluation of the State of Cure in a Tire," *Tire Science and Technology*, TSTCA, vol. 19, No. 4, Oct.–Dec., 1991, pp. 178–212.

(List continued on next page.)

*Primary Examiner*—Paul P. Gordon
*Assistant Examiner*—Sheela S. Rao
*Attorney, Agent, or Firm*—St. Onge Steward Johnston & Reens LLC

[57] ABSTRACT

A database of reversion cure constants is provided by measuring a physical property of a rubber formulation at two different temperatures as a function of time, calculating a set of cure constants for the rubber formulation which account for reversion, and storing the constants for later use either to optimize cure for a given process or of a given compound, or to assure quality of a raw compound. The invention also provides a curing press for optimizing cure including a mold, a heater, a temperature transducer, a computer and the database.

17 Claims, 9 Drawing Sheets

OTHER PUBLICATIONS

Isayev, A.I. and Deng, J.S., "Nonisothermal Vulcanization of Rubber Compounds," *Rubber Chemistry and Technology*, vol. 61, No. 2, 1988, pp. 340–361.

Deng, J.S. and Isayev, A.I., "Injection Molding of Rubber Compounds: Experimentation and Simulation," *Rubber Chemistry and Technology*, vol. 64, No. 2, 1991, pp. 296–324.

Deng, J.S., "Taking a Closer Look at the Modeling on Nonisothermal Curing Kinetics," presented at a meeting of the Rubber Division, American Chemical Society, Detroit, Michigan, Oct. 8–11, 1991 (Paper No. 55).

Burger, J., Burger, N., and Pogu, M., "Influence of Some Parameters on the Solution of a Thermal Model of Vulcanization," *Rubber Chemistry and Technology*, vol. 66, No. 1, 1992, pp. 19–22.

Chan, T.W., Shyu, G.D., and Isayev, A.I., "Reduced Time Approach to Curing Kinetics, Part I: Dynamic Rate and Master Curve from Isothermal Data," *Rubber Chemistry and Technology*, vol. 66, 1993, pp. 849–864.

Chan, T.W., Shyu, G.D., and Isayev, A.I., "Reduced Time Approach to During Kinetics, Part II: Master Curve from Nonisothermal Data," *Rubber Chemistry and Technology*, vol. 67, 1994, pp. 314–328.

Nordsiek, K.H., "Rubber microstructure and reversion," *Rubbercon 87*, Harrogate.

Dogadkin, B., Karmin, B., and Goldberg, I., "Kinetics and Optimum Phenomenon of Vulcanization," *Rubber Chemistry and Technology*, vol. 20, 1947, pp. 933–937.

Peter, J. and Heidemann, W., "A New Method for Determining the Vulcanization Characteristics of Rubber Compounds," *Rubber Chemistry and Technology*, vol. 31, 1958, pp. 105–116.

Chen, C.H., Collins, E.A., Shelton, J.R., and Koenig, J.L., "Compounding Variables Influencing the Reversion Process in Accelerated Curing of Natural Rubber," *Rubber Chemistry and Technology*, vol. 55, No. 4, 1982, pp. 1221–1232.

Bhowmick, A.K. and DE, S.K., "Dithiodimorpholine–Based Accelerator System in Tire Tread Compound for High–Temperature Vulcanization," *Rubber Chemistry and Technology*, vol. 52, No. 5, 1979, pp. 985–994.

Lyubchanskaya, L.I. and Kuzminskii, A.S., "The Degradation of Main Chains and Crosslinks in the Aging of Vulcanizates," *Rubber Chemistry and Technology*, vol. 34, 1961, pp. 922–924.

Blackman, E.J. and McCall, E.B., "Relationships Between the Structures of Natural Rubber Vulcanizates and Their Thermal and Oxidative Aging," *Rubber Chemistry and Technology*, vol. 43, No. 3, 1970, pp. 651–663.

Studebaker, Merton L., "Effect of Curing Systems on Selected Physical Properties of Natural Rubber Vulcanizates," *Rubber Chemistry and Technology*, vol. 39, No. 5, 1966, pp. 1359–1381.

Parks, C.R., Parker, D.K., Chapman, D.A., and Cox, W.L., "Pendent Accelerator Groups in Rubber Vulcanizates," *Rubber Chemistry and Technology*, vol. 43, No. 3, 1970, pp. 572–587.

Shankar, Uma, "Investigations of the Reversion of Vulcanized Rubber Under Heat," *Rubber Chemistry and Technology*, vol. 25, 1952, pp. 241–250.

Beilstein, G., "Some Aspects of High Temperature Vulcanization," *Rubber Chemistry and Technology*, vol. 34, 1961, pp. 319–333.

Russell, R., Smith, D.A., and Welding, G.N., "Kinetics of Thiazole–Accelerated Sulfur Vulcanization of Natural Rubber," *Rubber Chemistry and Technology*, vol. 44, 1971, pp. 1316–1325.

Redding, R.B. and Smith, D.A., "Oberall Kinetics of Natural Rubber Vulcanization at High Temperatures," I. Review of Investigation TEchniques, Methods, and Previous Results of Kinetic Analysis, *Rubber Chemistry and Technology*, vol. 44, 1971, pp. 1316–1325.

Scott, K.W., Lorenz, O., and Parks, Carl L., "Network Degradation Accompanying the Vulcanization of Natural Rubber with a Sulfur–Diphenylguanidine System," *J. Applied Poly. Sci.*, vol. 8, 1968, pp. 2909–2922.

Dinges, U., Westenberger, H., and J. Schnetger, "Computer–Aided Optimization of the Vulcanization Process," Bayer AG, Bayerwerk, 5090 Leverkusen, Germany.

Elandt–Johnson, R.C. and Johnson, N.L., "Survival Models and Data Analysis," J. Wiley and Sons, Inc., N.Y., 1980.

Gnedenko, B., Beliaev, Y., Soloviev, A., "Methodes mathematiques en theorie du fiailite," Mir Moscow, 1972.

Mathcad PLUS 5.0, MathSoft Inc., Cambridge, Mass.

Seber, G.A.F., Wild, C.J., "Nonlinear Regression," J. Wiley and Sons, Inc., N.Y., 1989.

Kende, I., Pickering, T.L., and Tobolsky, A.V., "The Dissociation Energy of the Tetrasulfide Linkage," *J. Amer. Chem. Soc.*, vol. 87, 1965, p. 5582.

Conant, F.S. and Claxton, W.E., "Cepar Measurements of curing Constants, Continuous Measurements of the Cure Rate of Rubber," *ASTM Special Technical Publication*, No. 383, 1965, p. 36.

Communication dated Aug. 27, 1996 transmitting the European Patent Application Search Report.

Dinges, et al, "Computer–unterstützte Optimierung des Vulkanisationsprozesses", 993 Kautschuk+Gummi Kunststoffe 46(1993)Oktober, No. 10, Heidelberg, DE, pp. 805–811.

Deak, L., et al, "Testing and optimsing the vulcanisation process of rubber tyres", Interntl.Poly.Science Tech., 18:No.3: 26–31.

COMPOUND N

| TEMP., °C | 140 | 150 | 160 | 170 |
|---|---|---|---|---|
| $\Gamma_o$, dN × m | 3.39 | 3.22 | 3.04 | 2.72 |
| $\Gamma_e$, dN × m | 14.83 | 14.32 | 13.35 | 11.91 |
| n | 3.16 | 3.04 | 2.84 | 2.56 |
| $K^n(sec^{-1})^n$ | $7.727 \times 10^{-4}$ | $14.51 \times 10^{-4}$ | $27.50 \times 10^{-4}$ | $51.25 \times 10^{-4}$ |
| $K_\gamma$, $sec^{-1}$ | 0 | 0 | 0 | 0 |
| SL | 1 | 1 | 1 | 1 |
| ERROR | 0.25 | 0.23 | 0.19 | 0.12 |
| CORR. COEFF | 0.996 | 0.997 | 0.997 | 0.998 |

COMPOUND R

| TEMP., °C | 140 | 150 | 160 | 170 |
|---|---|---|---|---|
| $\Gamma_o$, | 3.85 | 3.46 | 3.06 | 3.57 |
| $\Gamma_e$, | 33.34 | 34.64 | 36.31 | 38.79 |
| n | 1.71 | 1.58 | 1.34 | 1.17 |
| $K^n(sec^{-1})^n$ | $8.885 \times 10^{-4}$ | $17.42 \times 10^{-4}$ | $31.97 \times 10^{-4}$ | $59.68 \times 10^{-4}$ |
| $K_\gamma$, $sec^{-1}$ | 0 | $1.160 \times 10^{-4}$ | $3.553 \times 10^{-4}$ | $10.30 \times 10^{-4}$ |
| SL | 1 | 0.685 | 0.653 | 0.600 |
| ERROR | 0.51 | 0.44 | 0.44 | 0.45 |
| CORR. COEFF | 0.997 | 0.998 | 0.997 | 0.996 |

FIG. 6

SYSTEM FOR OPTIMIZING CURE ASSURING QUALITY OF REVERSION SUSCEPTIBLE RUBBER ARTICLES

This is a continuation of application Ser. No. 08/408,148 filed on Mar. 20, 1995 now patented U.S. Pat. No. 568,015

FIELD OF THE INVENTION

The invention relates to a system for optimizing the cure cycle and/or for assuring the quality of reversion susceptible rubber articles.

BACKGROUND OF THE INVENTION

During vulcanization a rubber compound changes from a relatively weak, viscoelastic liquid to a relatively strong viscoelastic solid. This remarkable transformation in properties enables rubber formulations to be molded and cured to produce many useful articles. Probably the most useful rubber article is represented by the tire, however, the invention may also be used in the manufacture and quality control of other rubber articles.

It is well known that overcure of many tire and other rubber compounds results in reversion. This effect is directly observed as a disadvantageous decrease in modulus relative to the optimum value.

Most of the cure models presently used by the rubber industry do not account for reversion. Rather, they predict a monotonically increasing cure versus time profile. A particularly popular model is the Kamal model. The Kamal model relates the rate of cure to two rate constants $K_1$ and $K_2$, and two adjustable parameters m and n (Kamal, M. R., Sourour, S., and Ryan, M., "Integrated Thermo-Rheological Analysis of the Cure of Thermosets," 31st *Annual Technology Conference, SPE*, 187, Montreal, Canada, May 1973; Malkin, A. Y., "The Macrokinetics and Rheokinetics of the Hardening of Oligimers," *Russian Chemical Reviews*, Vol. 54, No. 3, 1985, p. 293; Kamal, M. R. "Thermoset Characterization for Moldability Analysis," *Polymer Engineering and Science*, Vol. 14, No. 3, 1974, p.231):

$$\frac{d\chi(t)}{dt} = (K_1 + K_2 \chi^m)(1 - \chi^n) \quad (1)$$

where X (t) is the degree of cure at time t. Usually t is the current time minus an apparent induction time. With $K_2$ and $K_1$ set to zero and with n set to one equation (1) reduces to the common first order law that has been reported by several authors (Conant, F. S. and Claxton, W. E., "Cepar Measurements of Curing Constants, Continuous Measurements of the Cure Rate of Rubber," *ASTM Special Technical Publication No. 383*, 1965, p.36; Smith, T. W. "Method and Apparatus for Controlling the Cure of a Rubber Article," U.S. Pat. No. 3,819,915 (1974); Gehman, S. D., Maxey, F. S., and Ogilby, S. R., "Vulcameter Determination of Best Cure," *Rubber Chemistry and Technology*, Vol. 38, No. 4,1965, pp.757–768). Toth, Chang, and Zanicelli found that with $K_1$ equal to 0, m equal to ½, and n equal to 1, good agreement between predicted and observed torque-time traces were obtained on many compounds ("Finite Element Evaluation of the State of Cure in a Tire," *Tire Science and Technology, TSTCA*, Vol. 19, No. 4, October–December, 1991, pp.178–212).

Setting $K_1$ equal to zero reduces equation (1) to the model proposed by Piloyan, et al. (Nature 212, 1966, p.1229). ("Nonisothermal Vulcanization of Rubber Compounds," *Rubber Chemistry and Technology*, Vol. 61, No. 2,1988, pp. 340–361); Deng and Isayev ("Injection Molding of Rubber Compounds: Experimentation and Simulation," *Rubber Chemistry and Technology*, Vol. 64, No. 2, 1991, pp.296–324); Deng ("Taking a Closer Look at the Modeling on Nonisothermal Curing Kinetics," presented at a meeting of the Rubber Division, American Chemical Society, Detroit, Mich., Oct. 8–11, 1991 (Paper No. 55)); Burger, Burger, and Pogu ("Influence of Some Parameters on the Solution of a Thermal Model of Vulcanization, "*Rubber Chemistry and Technology*, Vol 66, No. 1, 1992, pp.19–29); and Chan, Shyu, and Isayev ("Reduced Time Approach to Curing Kinetics, Part I: Dynamic Rate and Master Curve from Isothermal Data," *Rubber Chemistry and Technology*, Vol. 66, 1993, pp.849–864; Chan, T. W., Shyu, G. D., and Isayev, A. I., "Reduced Time Approach to Curing Kinetics, Part II: Master Curve from Nonisothermal Data," *Rubber Chemistry and Technology*, Vol. 67, 1994, pp. 314–328), have employed special forms of Piloyan's equation in their work.

None of the models discussed thus far take into account the possibility of reversion. It is generally thought that reversion results mainly from a loss of polysulfidic crosslinks and, to a lesser extent, the scission of main network chains. The rate of reversion is a function of the compound composition and, especially, the temperature, and ambient conditions. The composition variables include the amount of sulfur, level and type of accelerator, e.g., type of crosslink, filler, and elastomer (Nordsiek, K. H., "Rubber microstructure and Reversion," *Rubbercon 87*, Harrogate; Dogadkin, B., Karmin, B., and Goldberg, I., "Kinetics and Optimum Phenomenon of Vulcanization," *Rubber Chemistry and Technology*, Vol. 20, 1947, pp.933–937; Peter, J. and Heidemann, W., "A New Method for Determining the Vulcanization Characteristics of Rubber Compounds," *Rubber Chemistry and Technology*, Vol. 31, 1958, pp.105–116; Chen, C. H., Collins, E. A., Shelton, J. R., and Koenig, J. L., "Compounding Variables Influencing the Reversion Process in Accelerated Curing of Natural Rubber," *Rubber Chemistry and Technology*, Vol. 55, No. 4, 1982, pp.1221–1232; Bhowmick, A. K. and DE, S. K., "Dithiodimorpholine-Based Accelerator System in Tire Tread Compound for High-Temperature Vulcanization," *Rubber Chemistry and Technology*, Vol. 52, No. 5, 1979, pp.985994; Lyubchanskaya, L. I. and Kuzminskii, A. S., "The degradation of Main Chains and Crosslinks in the Aging of Vulcanizates," *Rubber Chemistry and Technology*, Vol. 34, 1961, pp.922–924; Blackman, E. J. and McCall, E. B., "Relationships Between the Structures of Natural Rubber Vulcanizates and Their Thermal and Oxidative Aging," *Rubber Chemistry and Technology*, Vol. 43, No. 3, 1970, pp.651–663; Studebaker, Merton L., "Effect of Curing Systems on Selected Physical Properties of Natural Rubber Vulcanizates," *Rubber Chemistry and Technology*, Vol. 39, No. 5, 1966, pp.1359–1381; Parks, C. R., Parker, D. K., Chapman, D. A., and Cox, W. L., "Pendent Accelerator Groups in Rubber Vulcanizates," *Rubber Chemistry and Technology*, Vol. 43, No. 3, 1970, pp. 572–587).

Reversion degrades physical properties such as modulus, fatigue life, and the like. Since the reversion rate may rise drastically as the temperature increases it may happen that the physical-mechanical properties obtained from a short time, high temperature cure cycle are inferior to those obtained from a relatively long time, low temperature cure cycle.

A search of the literature shows that only a few authors have even attempted to include reversion in their proposed cure kinetics models. Interestingly, Shankar only considered the reversion portion of the cure and concluded, from swelling measurements, that the crosslink density decreased exponentially with time (Shankar, Uma, "Investigations of the Reversion of Vulcanized Rubber Under Heat," *Rubber Chemistry and Technology*, Vol. 25, 1952, pp.241–250).

Beilstein proposed that stable and unstable crosslinks are formed and that only the latter break down, thus implying a limiting value for the degree of cure ("Some Aspects of High Temperature Vulcanization," *Rubber Chemistry and Technology*, Vol. 34, 1961, pp.319–333). Beilstein assumed first order kinetics for the two forward reactions and also first order kinetics for the reversion reaction that destroys the unstable crosslinks ("Some Aspects of High Temperature Vulcanization," *Rubber Chemistry and Technology*, Vol. 34, 1961, pp.319–333).

Several authors have presented models that account for a marching modulus type cure subsequent to a pronounced reversion (Russell, R., Smith, D. A., and Welding, G. N., "Kinetics of Thiazole-Accelerated Sulfur Vulcanization of Natural Rubber," *Rubber Chemistry and Technology*, Vol. 36, No. 3, 1963, pp.835–843; Redding, R. B. and Smith, D. A., "Overall Kinetics of Natural Rubber Vulcanization at High Temperatures, I. Review of Investigation Techniques, Methods, and Previous Results of Kinetic Analysis," *Rubber Chemistry and Technology*, Vol. 44, 1971, pp.1316–1325). Their model assumes the overall cure curve results from the sum of three concurrent reactions:

a. first order insertion of crosslinks
 b. first order destruction of crosslinks
 c. a slow, zero order crosslinking reaction.

Scott and coworkers presented a simple, two rate constant model for reversion type cures ("Network Degradation Accompanying the Vulcanization of Natural Rubber with a Sulfur-Diphenylguanidine System," *J. Applied Poly. Sci.*, Vol. 8, 1964, pp.2909–2922). Essentially the same model was used recently by Dinges, Westenberger, and Schnetger in a study regarding computer-aided optimization of a vulcanization process ("*Computer-Aided Optimization of the Vulcanization Process*," Bayer AG, Bayerwerk, 5090 Leverkusen, Germany). This particular model is easily cast in terms of rheometer torque readings if one assumes changes in isothermal torque values are proportional to changes in crosslink density.

None of these known models accurately predicts optimum cure for cases with and without reversion, while simultaneously offering a reasonable kinetic interpretation of some basic mechanism of the vulcanization process.

Advanced tire manufacturers nonetheless use these flawed cure kinetics models for setting optimum cure cycles. The modern cure process uses expensive, high technology equipment, consumes energy, and strongly affects the material properties. A temperature history of the cycle is used in an attempt to optimize the cure according to the model. An "optimized cure" insures superior tire compound properties in a cost competitive manner.

U.S. Pat. No. 4,551,807 discloses a cure control method utilizing a model which does not account for reversion.

U.S. Pat. No. 4,371,483 discloses a vulcanizing process utilizing a model which assumes no reversion and no induction time, and which is a special case of the '807 patent model.

U.S. Pat. No. 3,819,915 discloses a method for controlling the cure of a rubber article according to a model which accounts for an induction time but not for reversion and is a special case of the '483 patent model.

U.S. Pat. No. 5,055,245 discloses a method for controlling tire cure via temperature measurements of boundary conditions which are then used to predict temperature profiles throughout the tire. Cure state is then predicted by an Arrhenius approach which does not account for reversion.

U.S. Pat. No. 4,34,142 discloses a rubber molding press controlled by an optimum cure time continuously recalculated according to an Arrhenius approach.

U.S. Pat. No. 4,819,177 discloses a method of curing thin, rubber articles such that prediction of temperature gradients within the articles is unnecessary and only mold set temperature is monitored and controlled.

U.S. Pat. Nos. 4,810,438 and 5,345,397 disclose systems for controlling the cure of fiber-reinforced composites within autoclaves.

U.S. Pat. No. 5,207,956 discloses a method of cure control via in-line measurement of sound velocity which is related to modulus.

What is desired, therefore, is a system for optimizing the cure cycle and/or for assuring the quality of rubber articles utilizing a model which accounts for reversion.

SUMMARY OF THE INVENTION

Accordingly, it is an object of the invention to provide a model for the cure of a rubber article which accounts for reversion.

Another object of the invention is to provide a system using the above model for tuning the curing process of a given compound to achieve optimized cure for a rubber article.

A further object of the invention is to provide a system using the above model for altering a compound to achieve optimized cure with a given process.

Still another object of the invention is to provide a system using the above model for analyzing the quality of a raw rubber compound before it is used to manufacture a rubber article with a non-optimized cure.

Yet a further object of the invention is to provide a system of the above character for aiding to diagnose production problems causing deviation from optimized cure in finished articles.

Yet another object of the invention is to provide a curing press for manufacturing an article from a rubber formulation with an optimized cure.

These and other objects of the invention are achieved by provision of a method of creating a database of reversion cure constants comprising measuring a physical property of each formulation at two different temperatures as a function of time, calculating a set of cure constants for the rubber formulation which account for reversion from the physical property versus time profiles, and storing the constants.

In another aspect the invention relates to a method for optimizing cure of a rubber compound using the database and comprising determining a temperature-time profile of a curing process, and reducing the profile and the constants for the compound to a succession of isothermal cases for determining whether cure is optimized.

In another aspect the invention relates to a method for assuring quality using the database and comprising preparing a sample, measuring the sample at a given temperature as a function of time, applying a reversion model to the measured data and comparing measured constants with predicted constants for the sample.

The invention also provides a curing press for optimizing cure including a mold, a heater, a temperature transducer, a computer and the database.

The invention and its particular features and advantages will become more apparent from the following detailed description considered with reference to the accompanying drawings.

BRIEF DESCRIPTION OF THE DRAWINGS

FIG. 6 is a table summarizing constants for Compounds N and R derived using a predictive model for reversion type cures in accordance with the invention.

DETAILED DESCRIPTION OF THE INVENTION

Figure 1:
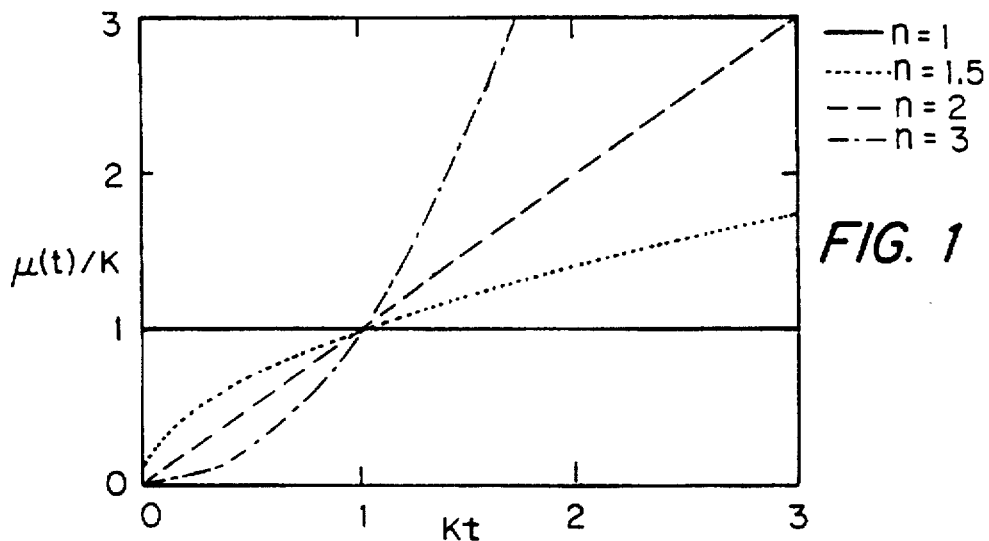
FIG. 1 is a plot of μ(t) versus Kt at different values of n.

Before describing use of the reversion model to optimize cure and assure quality of manufactured rubber products, we will explain the mathematical derivation of our reversion model.

A. Non-reverting Cures

We follow an approach that is well known in the study of phenomena that involve transformation of populations from one state to another. Some examples are the development of mortality profiles (transformation from living to dead) (Eland-Johnson, R. C. and Johnson, N. L., "*Survival Models and Data Analysis*," J. Wile and Sons, Inc., N.Y., 1980) and the aging of industrial products (transformation from working to broken) (Gnedenko, B., Beliaev, Y., Soloviev, A., "*Methodes methematiques en theorie de le fiabilite*," Mir Moscow, 1972). The basic hypothesis is that the speed at which a species A changes state relative to the amount of A still to be transformed, follows some regular pattern. Thus, the Basic law of the transformation phenomenon is of the kind:

$$\mu(t) = -\frac{dA}{dt} * \frac{1}{A} \qquad (2)$$

For example, for the survival analysis of human populations equation (2) becomes the Gompertz law [30]:

$$\mu(x) = D\exp(x/E) \qquad (3)$$

where the quantity μ(x) is defined the "force of mortality".

In reliability theory, the failure of a population of industrial products is well ruled by the following expression (Weibull law (Gnedenko, B., Beliaev, Y., Soloviev, A., "*Methodes methematiques en theorie de le fiabilite*," Mir Moscow, 1972)):

$$\mu(x) = Ft^n \qquad (4)$$

The quantity μ(x) is defined, in this case, as the hazard function.

Inspection of the rheometer cure (or other test properties such as sonic velocity, differential scanning calorimeter, dielectrometer and the like, which can be related to cure state) curves for the cases with no reversion suggests that the reaction(s) that transform sulfur from the free state to the crosslinked one can well be described by an assumption of the kind in equation (4). If we let S indicate the current amount of sulfur, $S_o$ denote the initial amount, and C the amount that is crosslinked, then one can write:

$$S \to C$$

$$S_o - S = pC \qquad (5)$$

where p adjusts for the stoichiometry of the transformation. The limiting value of C becomes $C_e = S_o/p$.

According to the above discussion, we can define the following quantity:

$$\mu(t) = -\frac{dS}{dt} * \frac{1}{S} = \frac{dC}{dt} * \frac{1}{C_e - C} \qquad (6)$$

The last equation defines the specific rate of disappearance of S or the specific growth rate of C.

If we now introduce the Weibull law the quantity on the left side of equation (6) becomes:

$$\mu(t) = K(Kt)^{n-1} \qquad (b\ 7)$$

where n is equal to or greater than one. K is a rate constant that will be shown below to obey the Arrhenius equation. Thus, the rate of formation of C(t) is given by:

$$\frac{dC(t)}{dt} = (C_e - C)K(Kt)^{n-1} \qquad (8)$$

When n is equal to one the last equation reduces to the simple first order cure law. In this case the overall rate constant is equal to K, i.e., μ is independent of time under isothermal conditions. However, when n is greater than one the last equation implies a zero cure rate when the time t is zero. In conventional derivation of chemical kinetic equations this would be not allowed. However, we recognize that the molecular details of how an S becomes a C are extremely complex. The conversion of free sulfur to crosslinks probably involves many intermediate species, giving rise to a large sequence of relatively simple kinetic steps. Hence, the "regular pattern" mentioned above is taken to be an apparent time-dependent rate constant, μ(t), whose validity will be judged by how well it will fit the experimental data.

Integration of equation (8) yields:

$$C(t) = C_e \left\{ 1 - e^{-\frac{(Kt)^n}{n}} \right\} \qquad (9)$$

The quantity $X(t) = C(t)/C_e$ is defined to be the degree of conversion (cure). The quantity $C_e$ is the asymptotic value of C(t) observed as the time approaches infinity.

FIG. 1 depicts a plot of μ(t) versus Kt. Each curve corresponds to a different value of n. It is seen that as n becomes greater than 1 (first order kinetics) the specific speed of transformation gets smaller and smaller for Kt less than 1 and the opposite happens for values of Kt greater than 1.

Figure 2:
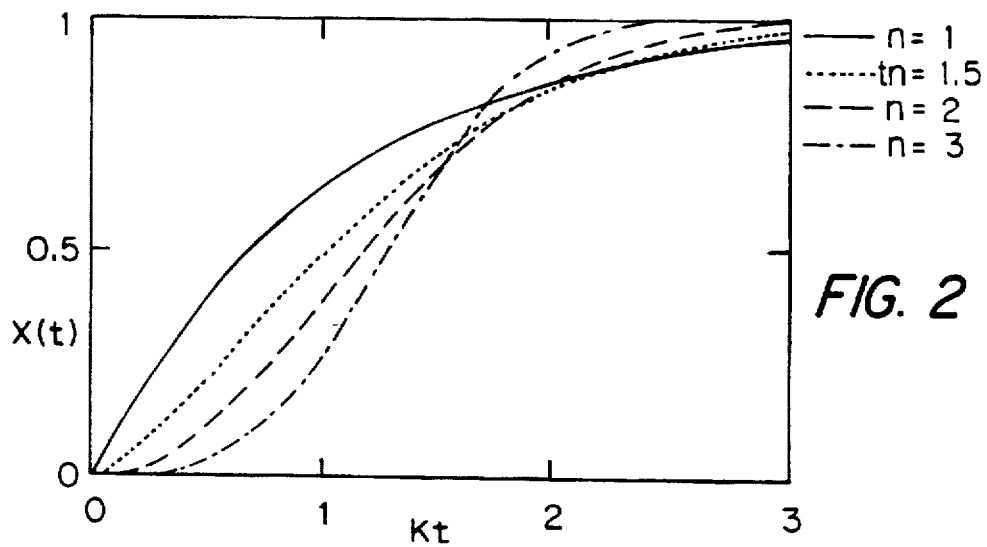
FIG. 2 is a plot of X(t) versus Kt at different values of n.

The consequence of this on the degree of cure is shown in FIG. 2, where again the independent variable is Kt. As n increases the shape of X(t) becomes flatter near the origin, creating a delay that suggests a traditional "induction time". It is also seen that with increasing n the lowest "starter" attained the highest degree of cure after about Kt=2.

Figure 3:
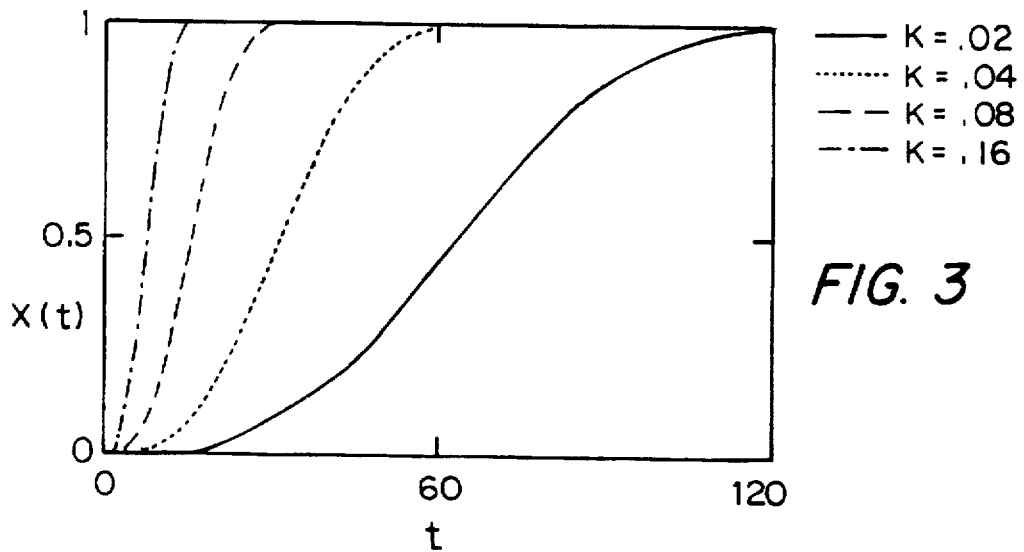
FIG. 3 is a plot of X(t) versus t at different values of K.

FIG. 3 shows how the degree of cure changes as K assumes different values but with n set to a constant value equal to 4. The K values are typical for experimental values observed at 140, 150, 160, and 170 degrees C.

B. Reverting Cures For cures that exhibit reversion we assume the following simple scheme:

$S \rightarrow C_\alpha$ formation of strong crosslinks $S \rightarrow C_\beta$ formation of weak crosslinks $C_\beta \rightarrow P$ loss of weak crosslinks where each of the specific rate constants for the steps above are denoted as:

$$\mu_\alpha(t) = K_\alpha (K_\alpha t)^{n-1} \tag{10}$$

$$\mu_\beta(t) = K_\beta (K_\beta t)^{n-1}$$

$$\mu_\gamma(t) = K_\gamma (K_\gamma t)^{n-1}$$

According to the scheme shown above one can write the rate of transformation of S as:

$$\frac{dS(t)}{dt} = -(\mu_\alpha(t) + \mu_\beta(t))S(t) \tag{12}$$

Integration of the last equation yields:

$$S(t) = S_o e^{-\frac{(K_\alpha^n + K_\beta^n)t^n}{n}} \tag{13}$$

where $S_o$ is the concentration of S at t=0. Let C(t) denote the total concentration of crosslinks. Thus, $$C(t) = C_\alpha(t) + C_\beta(t) \tag{14}$$

The rate of formation of the strong links is given by:

$$\frac{dC_\alpha(t)}{dt} = \mu_\alpha(t)S(t) \tag{15}$$

The rate of formation of the weak crosslinks is given by:

$$\frac{dC_\beta(t)}{dt} = \mu_\beta(t)S(t) - \mu_\gamma(t)C_\beta(t) \tag{16}$$

Upon substitution of equation (13) into equation (15) and into equation (16) the integration of the last two equations is easily carried out. The initial concentrations of weak and strong links are taken to be zero. The degree of cure is $X(t) = C(t)/S_o$. Thus, $$\chi(t) = \tag{17}$$

$$\frac{K_\alpha^n}{K^n}\left(1 - e^{-\frac{(Kt)^n}{n}}\right) + \frac{K_\beta^n}{K^n - K_\gamma^n}\left(e^{-\frac{(K_\gamma t)^n}{n}} - e^{-\frac{(Kt)^n}{n}}\right)$$

where, to gain economy in writing we have defined $K^n$ to be:

$$K^n = K_\alpha^n + K_\beta^n \tag{17a}$$

Thus, $X(0)=0$ and $X(\infty)=1$ when $K_\gamma=0$, as required.

For sufficiently long time X(t) is equal to the fraction:

$$SL = \frac{K_\alpha^n}{K_\alpha^n + K_\beta^n}$$

for the reverting cure case. This quantity may be considered as representing the fraction of crosslinks remaining after reversion is complete, i.e., the fraction of strong links.

We relate the degree of cure to the corresponding rheometer torque value in the following manner.

Consider the torque to be the sum of a viscous component and a component resulting from chemical formation of crosslinks. Thus, $$\Gamma(t) = \Gamma_v(t) + v_c(t) \tag{18}$$

$$\Gamma(t) = \Gamma_v(t) + v_e X(t)$$

For the viscous component, $\Gamma(t)$, we impose the following constraints:

$$\Gamma_v(0) = \Gamma_o \tag{19}$$

$$\Gamma_e(\infty) = 0$$

The component due to formation of crosslinks has the following properties:

$$\Gamma_c(0) = 0 \tag{20}$$

and, with the viscous component set to zero:

$$\Gamma_c(\infty) = \Gamma_e \tag{21}$$

We assume that the viscous component takes the form:

$$\Gamma_v(t) = e^{-\frac{ht^n}{n}} \tag{22}$$

where h is a constant. Recognizing that the derivative of $\Gamma(t)$ with respect to time is equal to zero when t=0 one easily obtains the following expression for h:

$$h = (K_\alpha^n + K_\beta^n)\frac{\Gamma_e}{\Gamma_0} \tag{23}$$

Combining equations 18, 22, and 23 yields the following expression for the isothermal torque-time profile:

$$\Gamma(t) = \Gamma_o e^{-(K_\alpha^n + K_\beta^n)\frac{\Gamma_e t^n}{\Gamma_o n}} + \Gamma_e \chi(t) \tag{24}$$

which includes six cure constants accounting for reversion $K_\alpha$, $K_\beta$, $K_\gamma$, $\Gamma_e$, $\Gamma_o$, and n.

C. The Curve Fitting Algorithm

The numerical approach followed to identify the coefficients and to verify the validity of the proposed model involved two stages.

In the first stage a commercially available, multipurpose software package, MATHCAD 5.0+ (MathSoft Inc. of Cambridge, Massachusetts), had been applied to isothermal data to test several preliminary versions and to fine tune the structure of the model. This stage has been particularly useful in generalizing equation (9) to the case with reversion.

After verifying that the model, equation (24), is acceptable from a numerical point of view (low error, high correlation) and sound from a physical point of view because it enables a reasonable interpretation of the overall chemical mechanism involved, an ad hoc curve fitting code was then developed.

Specifically, in the second stage a numerical algorithm able to automatically generate a first guess for the unknown constants and then begin an iteration process based on the Newton-Gauss and steepest descent methods. At each step a solution is found with both methods. Then a "line-search" finds a third solution that is the optimal between the first two solutions. In the literature the previous method is known as *"Powell's Hybrid Method"* (Seber, G. A. F., Wild, C. J., *"Nonlinear Regression,"* J. Wiley and Sons, Inc., N.Y., 1989).

The code has been written in GWBASIC and can run on any PC. A typical case with about 30 to 40 experimental torque-time data points requires no more than a few minutes of computation time with a 486 microprocessor (66 MHz). presently, about 80 isothermal cases have been analyzed with very good results.

D. Non-Isothermal Case

For each rheometer (or other physical property test) curve, six constants are obtained via the numerical algorithm described in the previous section: $K_\alpha$, $K_\beta$, $K_\gamma$, $\Gamma_e$, $\Gamma_o$, and n. Once the six constants have been calculated for several temperatures (minimum of two required), each one of them is expressed as a formula which describes their temperature dependence. We have found, for example, that the constants obey an Arrhenius type expression of the kind, $$K_\alpha = K_\alpha^o e^{-\frac{E_\alpha}{RT}} \qquad \Gamma_o = \Gamma_o^o e^{-\frac{E_o}{RT}} \qquad (25)$$

$$K_\beta = K_\beta^o e^{-\frac{E_\beta}{RT}} \qquad \Gamma_e = \Gamma_e^o e^{+/-\frac{E_e}{RT}}$$

$$K_\gamma = K_\gamma^o e^{-\frac{E_\gamma}{RT}} \qquad n = n^o e^{-\frac{E_n}{RT}}$$

allowing a simple representation of their respective temperature dependencies that can be found with a simple linear least squares procedure. Twelve constants are thus defined for the non-isothermal case $K_\alpha^o$ and $E_\alpha$, $K_\beta^o$ and $E_\beta$, $K_\gamma^o$ and $E_\gamma$, $\Gamma_o^o$ and $E_o$, $\Gamma_e^o$ and $E_e$, and $n^o$ and $E_n$. The twelve constants can also be obtained with a fitting algorithm that calculates them simultaneously from equations 24, 25 using as input a set of at least two temperature-time profiles. It is understood that other types of expressions representing temperature dependency may also be used.

These twelve constants make it possible to predict the torque and/or degree of cure for an arbitrary temperature-time profile using known numerical methods for reducing the general case to a succession of isothermal cases.

E. Comparison of Experimental and Predicted Rheometer Cure Profiles

The following comparisons are not intended to be restrictive of the invention but only to demonstrate that the model accurately predicts cure profiles for compounds having very different degrees of reversion.

A Monsanto Moving Die Rheometer (MDR), model 2000E was used to obtain the rheometer cure curves. The samples were run at 140, 150, 160, and 170 degrees C. The strain amplitude was set to +/−0.5 degrees arc at a frequency of 1.667 Hertz.

The two compounds reported on here are both accelerated, sulfur cure recipe, carbon black-loaded, elastomers. The first compound, denoted compound N, exhibits essentially no reversion upon curing. The second compound, denoted compound R, exhibits a significant degree of reversion, especially at elevated temperatures.

Figure 4:
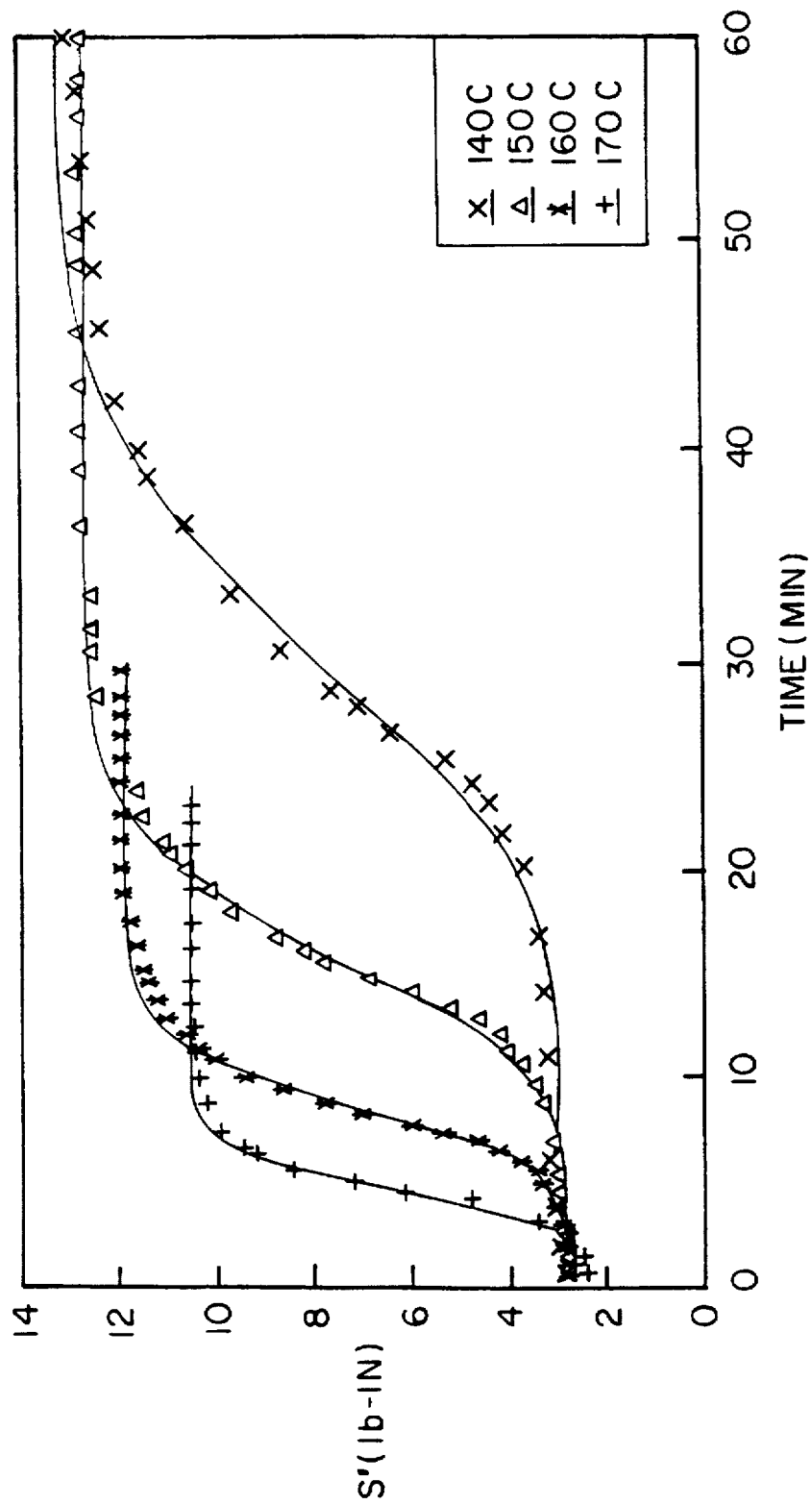
FIG. 4 is a comparative plot of S' versus time for predicted and observed torque curves of Compound N at different temperatures.

FIG. 4 shows a comparison of the predicted cure curves (solid lines) versus the experimentally observed curves for compound N, the non-reverting compound. A similar comparison is shown in FIG. 5 for Compound R, the reverting compound.

Figure 5:
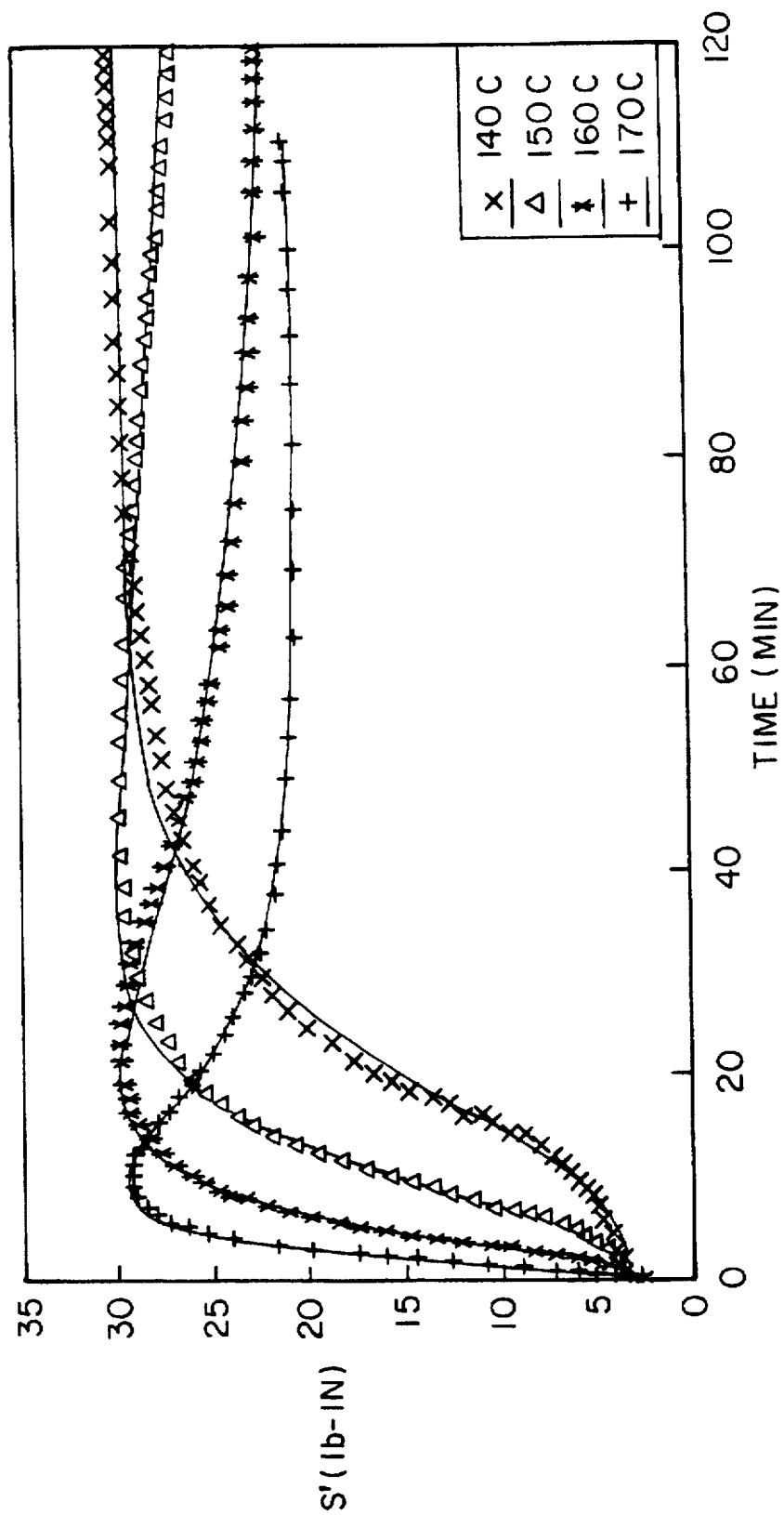
FIG. 5 is a comparative plot of S' versus time for predicted and observed torque curves of Compound R at different temperatures.

Inspection of FIGS. 4–5 shows that there is a slight, systematic difference between the shapes of the experimental and predicted torque curves. However, the overall "fit" is excellent and appears to improve with increasing temperature. Furthermore, the difference is within the usual batch to batch reproducibility observed in plant operations.

FIG. 6 is a table which lists the constants used to predict the curves, via equation (24), at each respective temperature. The constants which would be obtained via use of equation (25) were not used here. If those obtained from equation (25) were used, however, one would observe about equal, overall "goodness of fit".

Nevertheless, from the Arrhenius plots for the rate constants the following values of the activation energies were deduced:

| Compound: | N | R |
|---|---|---|
| $E_\alpha$, J/mole | $9.62*10^4$ | $7.91*10^4$ |
| $E_\beta$, J/mole | — | $10.97*10^4$ |
| $E_\gamma$, J/mole | — | $17.07*10^4$ |

The dissociation energy of the tetrasulfide linkage has been studied by a kinetic technique by Kende, Pickering, and Tobolsky ("The Dissociation Energy of the Tetrasulfide Linkage," J. *Amer. Chem. Soc.*, Vol. 87, 1965, p.5582). They suggested that the experimental activation energy may be equated to the dissociation energy of the sulfur-sulfur bond in methyl sulfide. The particular value they reported is $15.1*10^4$, $+/-1.5*10^4$ joules/mole. Our value of $E_\gamma=17.07*10^4$ joules/mole is in good agreement with the Tobolsky school. The latter reference also reviews the work of others in the field. Furthermore, the activation energies for the formation steps appear to be well within the range reported in the rubber literature. Consequently, we believe our model yields physically reasonable parameters.

Now, with reference to FIGS. 7–11, use of the reversion models represented by equation 24 in the isothermal case, with the addition of equation 25 in nonisothermal conditions, to optimize cure and control quality in accordance with the invention is described.

Figure 7:
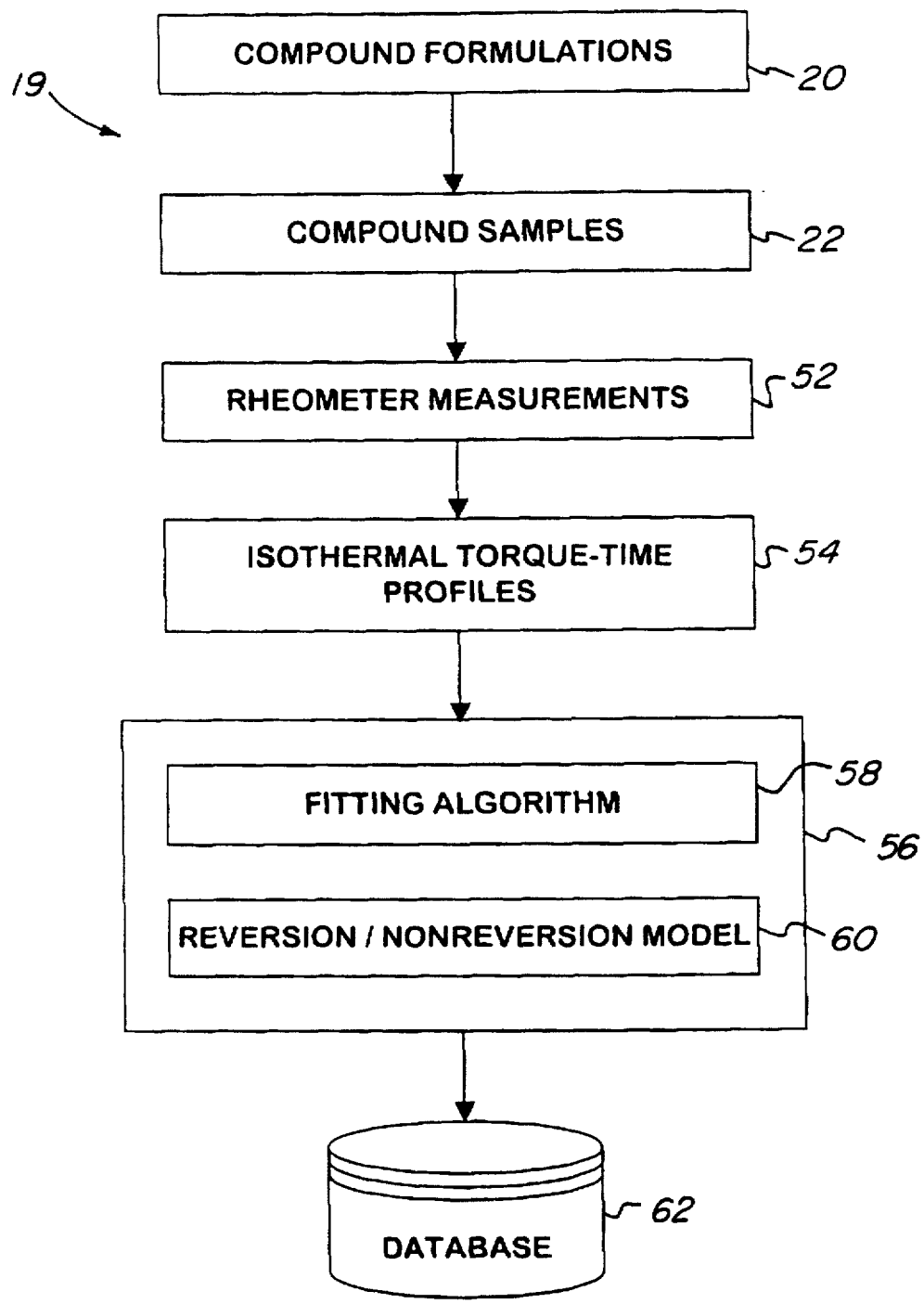
FIG. 7 is a block diagram illustrating creation of a database of constants for a myriad of rubber compounds derived using a predictive model for reversion type cures in accordance with the invention.

FIG. 7 depicts creation of a database of cure constants for later use to optimize cure and control quality of rubber articles. For each different rubber compound formulation 20, a raw rubber sample 22 is made. Torque (or other physical properties which may be related to cure state) measurements are made on the rubber samples at 52 with a rheometer to generate isothermal torque-time profiles 54 (see, e.g. FIGS. 4–5). A computer 56 is used to apply a curve fitting algorithm 58 to each profile 54 from which the six isothermal constants may be determined with equation 24, the isothermal case of reversion/nonreversion model 60.

Once the six constants have been determined at a minimum of two temperatures for a particular compound formulation 20, each of the constants can be expressed with a formula which describes their temperature dependence. Equation 25 represents this non-isothermal case of reversion/nonreversion model 60 from which the twelve non-isothermal constants can be determined. These twelve non-isothermal constants are then stored on database 62 for each compound formulation. It is understood that in the event only the isothermal constants will be necessary, the six constants may be stored on the database for each compound formulation.

Sets of the twelve constants collected and stored on database 62 can be used in two ways to optimize cure and control quality. First, the twelve constants can be combined with a given temperature to yield predicted values of the six isothermal constants for a comparison to empirically derived values of the constants at the given temperature. Second, the twelve constants can be combined using known numerical methods with a temperature-time profile of the curing process in order to determine state of cure.

Figure 8:
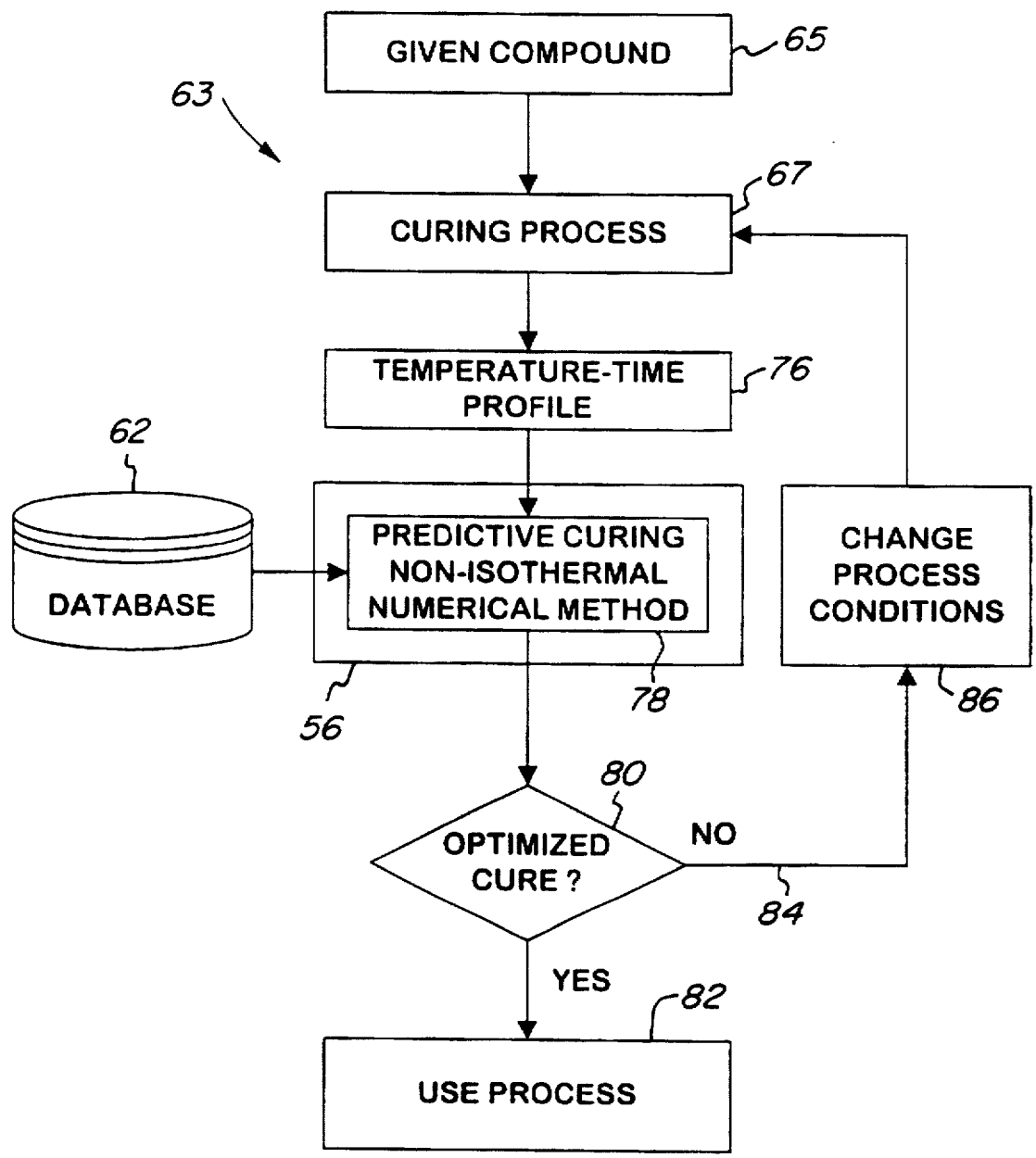
FIG. 8 is a block diagram depicting use of the database of FIG. 7 to derive an optimized curing process for a given compound.

Referring to FIG. 8, a system 63 for optimizing cure of a given compound 65 is illustrated. Given compound 65 may, for example, represent the formulation of a particular portion of a tire such as the sidewall, tread, subtread, or of another rubber product desired to be manufactured.

At 67, compound 65 is cured according to a process having particular ambient conditions, a particular type of mold or press, a particular type of mold/press heating means, a particular heat transfer medium, particular ramp up and cool down characteristics, and the like. In the case where they are tires 21, rubber article samples 22 are cured in a press 24 such as that illustrated in FIG. 11.

Press 24 comprises a mold unit 26 and a bladder unit 28. Bladder unit 28 includes a collapsible bladder 29 secured by upper and lower rings 30, 31 to a center post 32 supported within a sleeve 33. Lower ring 31 is connected to pipes 34, 36 for circulating heated fluid medium such as steam, gas or water through an inner space of bladder 29.

Mold unit 26 includes upper and lower mold halves 38, 40 arrayed between upper and lower platens 42, 44 for heating the mold. Platens 42, 44 include passages 46, 48 for circulation of heated fluid, e.g. via pipe 50. It is understood that other types of curing presses and/or molds having different features and capabilities may be used without departing from the scope of the invention. By way of example, but not limitation, the press may be electrically heated and the mold may be segmented into more than two parts.

Press 24 includes a plurality of temperature sensors 68, 70, 72, and 74 any one or more of which may be used to empirically determine a temperature-time profile 76 of curing process 67. It is understood that the temperature-time profile 76 may also be known, assumed or calculated for the curing process and compound, in which case no measurement need be taken nor any actual curing completed.

Computer 56 utilizes a known numerical method 78 with inputs of the twelve non-isothermal constants which account for reversion returned from database 62 for given compound 65, and a temperature-time profile for curing of compound 65 to reduce the general case to a succession of isothermal cases.

From this previous calculation, the degree of cure for any point in the rubber article where the temperature profile is given may be obtained. It is known at 80 to one skilled in the art whether the cure is optimized for the article. The overall cure of an article such as a tire having different compounds in different regions thereof (e.g. tread, sidewall, subtread) is optimized by optimizing cure of a single region of the tire or other article. Determination of which region of the article is most critical to optimize is known to one skilled in the art.

If cure is optimized, then system 63 ends at 82 and process 67 may be used to optimize cure for given compound 65. If, however, cure is not optimized, then system 63 branches along line 84 and changes 86 are made to curing process 67 in order to change its temperature-time profile 76. Change 86 may be a relatively simple matter of adjusting dwell time in the mold, maximum temperature of the mold and rates of mold heating/cooling, or it may require use of a different mold or press with different heating parameters or the use of a mold/press in a different ambient environment. For example, a molding process which is optimized for the summer months in a northern state may not be optimized for the same plant during the winter months.

Figure 9:
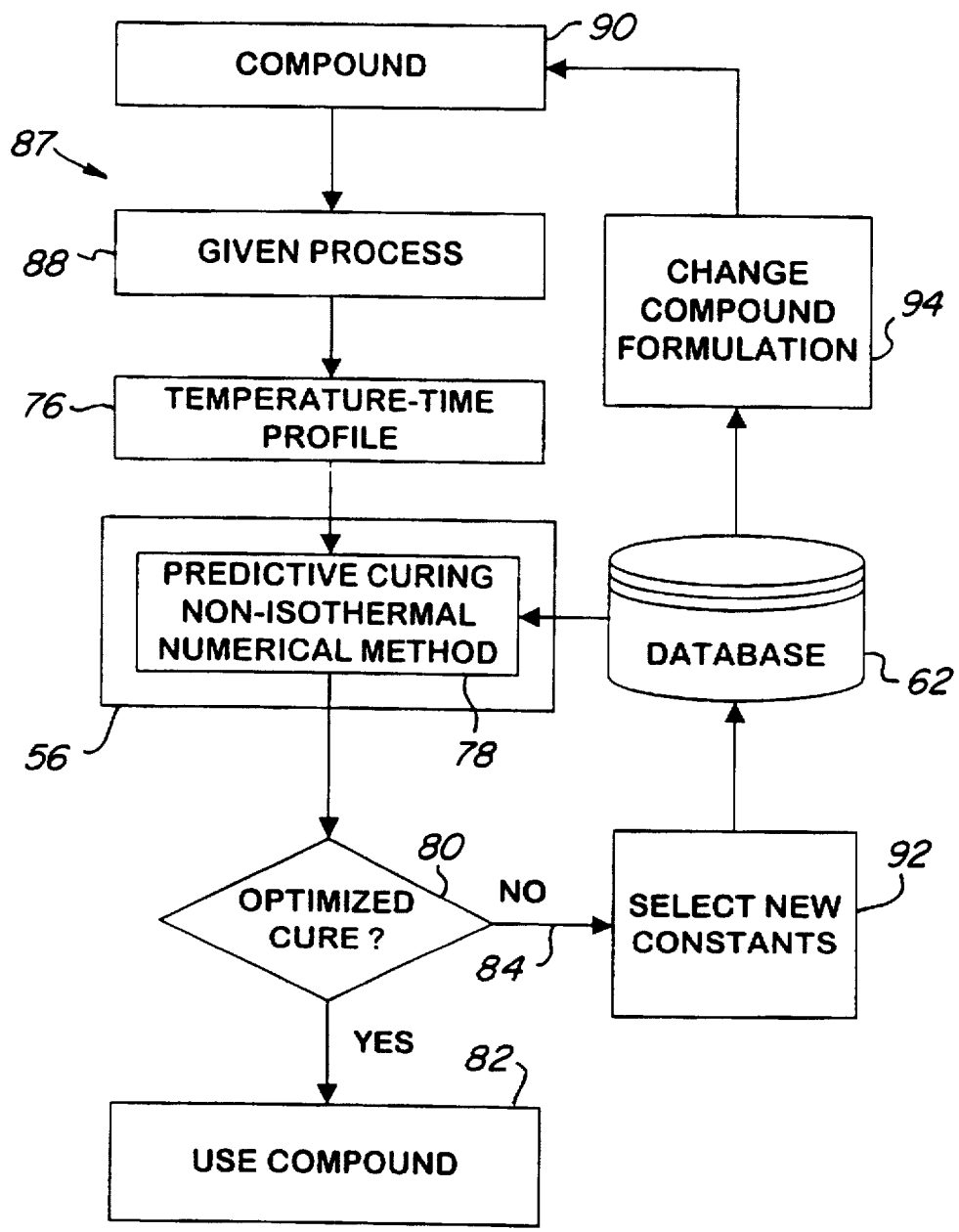
FIG. 9 is a block diagram depicting use of the database of FIG. 7 to derive a compound for achieving an optimized cure under a given process.

Referring now to FIG. 9, a system 87 for optimizing cure with a given curing process 88 is illustrated. Given process 88, for example, represents a particular curing press/mold and ambient conditions desired to be used to manufacture a tire or other rubber product.

At 90, a best guess compound is selected. This best guess is likely to become more and more accurate as database 62 grows and the operator becomes more familiar with its constants. Compound 90 level of cure can be predicted with the given process 88 and a temperaturetime profile which is measured—in the case of tires by sensors 68, 70, 72, and/or 74 (FIG. 11), for example. It is again understood that temperature-time profile 76 may also be known, assumed or calculated for the curing process and compound, in which case no measurements need be taken nor any actual curing completed.

As with system 63, Computer 56 utilizes a known numerical method 78 with inputs of the twelve non-isothermal constants which account for reversion returned from database 62 for given compound 65, and a temperature-time profile for curing of compound 65 to reduce the general case to a succession of isothermal cases.

As described above, it is known to one skilled in the art from the calculation at 80 whether the cure is optimized. If cure is optimized, then system 87 ends at 82 and no changes to the formulation of compound 90 need to be made to optimize cure for given curing process 88.

If, however, cure is not optimized, then system 87 branches along line 84 to select a new set of the non-isothermal constants 92 from database 62 representing a different or best second guess compound formulation 94. Possible changes to the rubber compound formulation include more or less carbon black, accelerator, sulfur, and the like. The best second guess is also likely to become more accurate as database 62 grows and the operator becomes more familiar with its contents.

Systems 63 (FIG. 8) and 87 (FIG. 9) permit rubber article manufacturers to optimize the cure of their rubber products, while accounting for possible reversion. An "optimized cure" provides the most complete cure with the lowest cure time and/or energy input, providing a tool to use plant facilities as economically as possible to produce high quality rubber products. It is understood that for articles such as tires which include multiple rubber compounds, cure of only a single compound or article region may be optimized and the selection of which compound this is and/or which region is optimized is made by one skilled in the art. It may be the case, e.g., that improving the cure of two compounds in a tire or other article may produce a better "optimized cure" product than optimizing the cure of one of these compounds to the detriment of the cure of the other.

Figure 10:
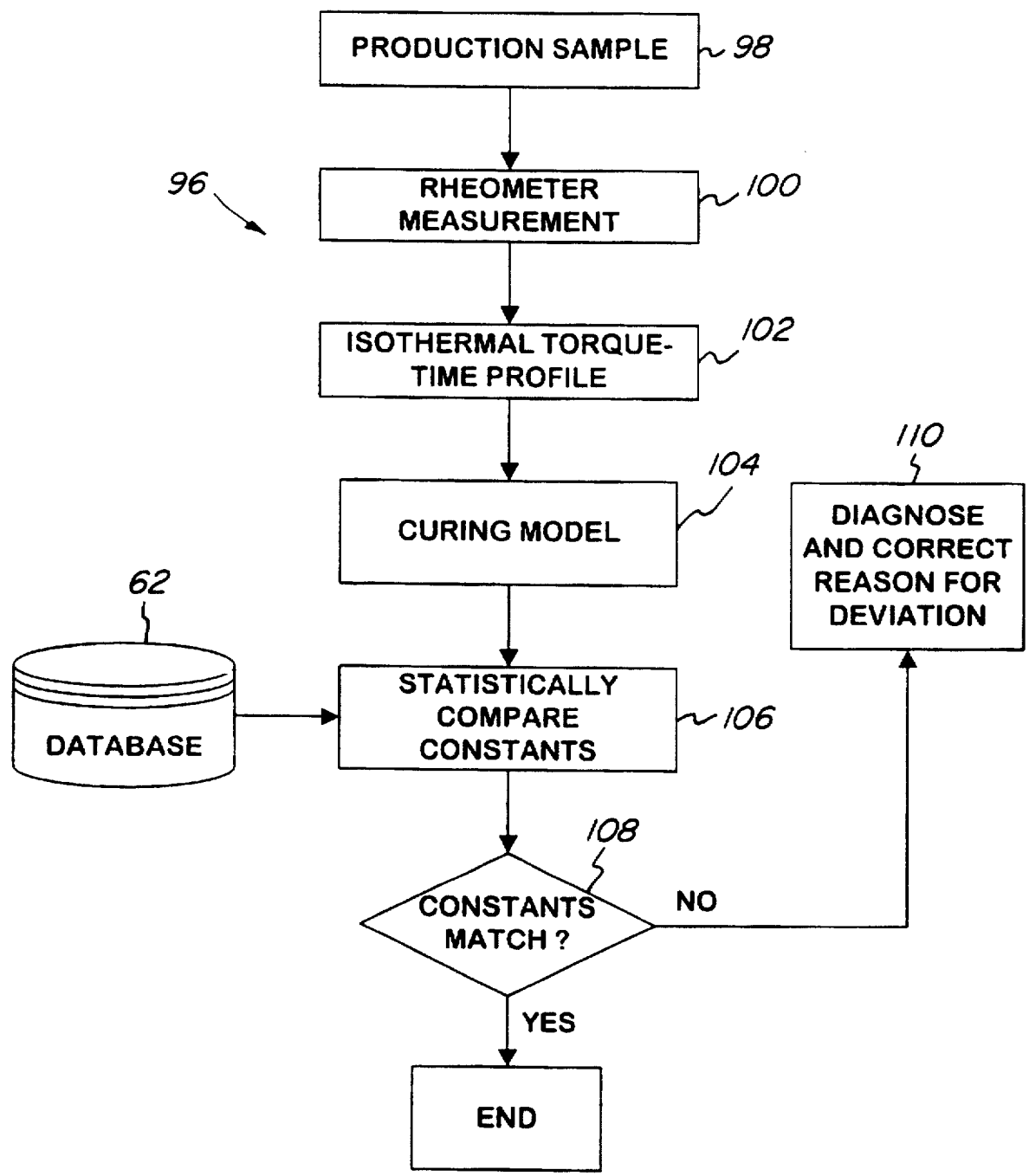
FIG. 10 is a block diagram depicting use of the database of FIG. 7 to assess the quality of a raw rubber compound before it is used to manufacture a rubber article with a non-optimized cure.
Figure 11:
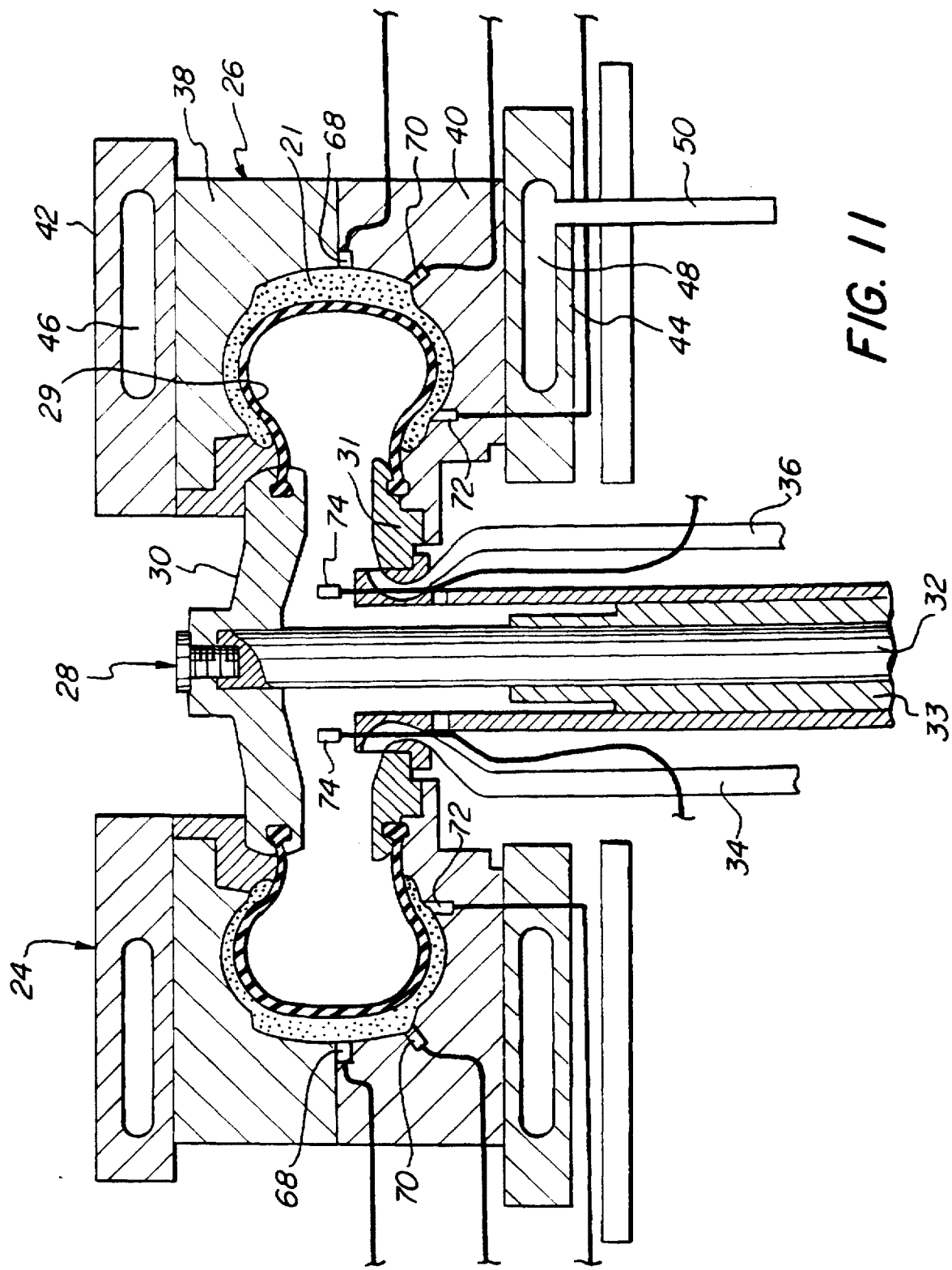
FIG. 11 is a cross-sectional schematic of a curing press for manufacturing tires according to the systems of FIGS. 8 and/or 9 for optimizing cure and/or the system of FIG. 10 for controlling quality of rubber articles.

Referring now to FIG. 10, the isothermal case of the reversion/nonreversion model 60 represented by equation 24 can be used in a quality assurance program 96 at a rubber article plant. A production rubber sample 98 may be selected from the production line for quality testing. Sample 98 is subjected to a rheometer test 100 at a given temperature to produce an isothermal torque-time profile 102. This test only takes a few minutes and can be done in real time before the rubber is used in a tire or other rubber article. It is understood that other physical property measurements may be substituted for the rheometer test, the only requirement being that the physical property tested be a function of cure state.

Applying the isothermal curing model of equation 24 to torque-time profiles 102 at 104 yields the six measured isothermal cure constants which account for reversion. The measured isothermal cure constants are then compared at 106 with the predicted isothermal cure constants for the formulation of the rubber compound and for the given temperature at which the rheometer measurements were taken.

Database 62 stores twelve non-isothermal constants for production sample 98 which may be converted to the isothermal constants using equation 25 and the given temperature.

If the measured and predicted values of the isothermal cure constants match at 108 then the continuing quality of the rubber articles is assured. If, however, the values of the measured and predicted isothermal constants do not match, then the reasons why continuing quality is not assured are diagnosed and corrective action may be taken at 110. Possible reasons include more or less than the expected amount of one of the rubber formulation's components, and deviations in preparation of the compound. As the database becomes more and more complete and the operator more knowledgeable, the database may be used to aid in diagnosing possible deviations from the expected formulation based upon the values of the constants obtained.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A method for creating a database of cure constants, which account for reversion, for later use to optimize cure of a rubber compound, comprising the steps of:
    providing a plurality of rubber samples, each sample having a particular rubber formulation;
    for at least two different temperatures, measuring a physical property which can be related to cure state of a sample of each different formulation as a function of time;
    calculating a set of cure constants for the rubber formulation which account for reversion from the physical property versus time profiles; and
    storing the set of cure constants on the database together with the corresponding rubber formulation.

2. A method for creating a database of cure constants, which account for reversion, for later use to optimize cure of a rubber compound, comprising the steps of:
    providing a plurality of rubber samples, each sample having a particular rubber formulation;
    for at least two different temperatures, measuring a physical property which can be related to cure state of a sample of each different formulation as a function of time;
    calculating at least one cure constant $K_\alpha^o$ defined in the following equation, $$K_\alpha = K_\alpha^o e^{-\frac{E_\alpha}{RT}}$$

for the rubber formulation which accounts for reversion from the physical property versus time profiles; and
    storing the cure constant $K_\alpha^o$ in the database together with the corresponding rubber formulation.

3. The method of claim 2, further comprising:
    calculating a cure constant $K_\beta^o$ defined in the following equation, $$K_\beta = K_\beta^o e^{-\frac{E_\beta}{RT}}$$

for the rubber formulation which account for reversion from the physical property versus time profiles; and
    storing the cure constant $K_\beta^o$ in the database together with the corresponding rubber formulation.

4. The method of claim 3, wherein the calculating steps comprise calculating a set of isothermal cure constants at each temperature for each sample from its physical property-time profile, expressing the isothermal constants with a formula which describes their temperature dependence, and calculating the cure constants $K_\alpha^o$ and $K_\beta^o$ for each rubber formulation.

5. The method of claim 4, wherein the measuring step comprises measuring torque with a rheometer.

6. The method of claim 4, further comprising the step of retrieving the cure constants $K_\alpha^o$ and $K_\beta^o$ from the database for a selected rubber formulation and combining them with a temperature-time profile of a curing process to predict state of cure of the selected rubber formulation.

7. A method for optimizing cure of a rubber compound, comprising the steps of:
    providing a database including non-isothermal cure constants $K_\alpha^o$ and $K_\beta^o$ defined in the following equations, $$K_\alpha = K_\alpha^o e^{-\frac{E_\alpha}{RT}}$$

$$K_\beta = K_\beta^o e^{-\frac{E_\beta}{RT}}$$

for the rubber compound which account for reversion;
    providing a curing process for the rubber compound;
    determining a temperature-time profile of the rubber compound for the curing process;
    reducing the temperature-time profile and the non-isothermal cure constants with numerical analysis into a succession of isothermal cases; and
    determining whether the curing process will optimize cure for the rubber compound.

8. The method of claim 7, wherein the profile determining step comprises measuring the temperature-time profile during curing of the rubber compound.

9. A method for assuring the quality of manufactured rubber articles, comprising the steps of:
    preparing a rubber sample according to a production formulation;
    measuring, at a given temperature, torque of the rubber sample as a function of time which can be related to cure state of the article;
    applying a curing model which accounts for reversion to the physical property measured as a function of time at a given temperature to generate a set of isothermal cure constants including $K_\alpha$ and $K_\beta$ defined in the following equations:

$$K_\alpha = K_\alpha^o e^{-\frac{E_\alpha}{RT}}$$

$$K_\beta = K_\beta^o e^{-\frac{E_\beta}{RT}}$$

retrieving a set of predicted cure constants for the production formulation at the given temperature from a database of predicted cure constants; and comparing the isothermal cure constants with the predicted cure constants to determine whether a rubber article produced with the production formulation will have an optimized cure.

10. The method of claim 9, wherein the retrieving step comprises retrieving predicted isothermal cure constants $K_\alpha^o$ and $K_\beta^o$.

11. The method of claim 9, wherein the retrieving step comprises the steps of:

retrieving predicted non-isothermal cure constants $K_\alpha^o$ and $E_\alpha^o$ and $K_\beta^o$ and $E_\beta^o$; and calculating isothermal cure constants $K_\alpha$ and $K_\beta$ from the predicted non-isothermal constants and the given temperature.

12. The method of claim 11, further comprising the step of searching the database of predicted cure constants at the given temperature with the generated isothermal cure constants to determine a formulation of the rubber sample.

13. A method of claim 11, further comprising the step of curing a portion of the rubber sample with a process determined to provide an optimized cure for the production formulation.

14. A curing press for manufacturing an article from a rubber formulation with an optimized cure, comprising:

a mold having at least two segments;

means for heating said mold;

a transducer for generating a signal indicative of a temperature within said mold; and a computer for receiving and storing the temperature indicative signal as a function of time and for storing at least one non-isothermal cure constant $K_\alpha$, defined in the following equation, $$K_\alpha = K_\alpha^o e^{-\frac{E_\alpha}{RT}}$$

for the rubber formulation, said computer for reducing the temperature-time profile and the cure constant to a succession of isothermal cases to determine whether the cure was optimized.

15. The curing press of claim 14, wherein the computer stores a non-isothermal cure constant $K_\beta$ defined in the equation $$K_\beta = K_\beta^o e^{-\frac{E_\beta}{RT}}$$

16. The curing press of claim 15, wherein the non-isothermal cure constants are calculated by measuring a sample of the rubber formulation with a rheometer for at least two different temperatures.

17. The curing press of claim 16, wherein said transducer is located within the mold in contact with a surface of the article being cured.

* * * * *